(12) United States Patent
Gupta et al.

(10) Patent No.: US 7,210,335 B2
(45) Date of Patent: May 1, 2007

(54) AUTOMATED CLAMP-ON SAMPLE CHAMBER FOR FLOW POROMETRY AND A METHOD OF USING SAME

(75) Inventors: Krishna M. Gupta, Ithaca, NY (US); Akshaya Jena, Ithaca, NY (US); William Wilson, Anniston, AL (US)

(73) Assignee: Porous Materials, Inc., Ithaca, NY (US)

( * ) Notice: Subject to any disclaimer, the term of this patent is extended or adjusted under 35 U.S.C. 154(b) by 0 days.

(21) Appl. No.: 11/105,705

(22) Filed: Apr. 15, 2005

(65) Prior Publication Data

US 2005/0229682 A1 Oct. 20, 2005

Related U.S. Application Data

(63) Continuation-in-part of application No. 10/826,095, filed on Apr. 16, 2004, now abandoned.

(60) Provisional application No. 60/570,515, filed on May 12, 2004.

(51) Int. Cl.
*G01N 15/08* (2006.01)
(52) U.S. Cl. .......................................................... 73/38
(58) Field of Classification Search ..................... None
See application file for complete search history.

(56) References Cited

U.S. PATENT DOCUMENTS

| | | | |
|---|---|---|---|
| 2,465,948 A | 3/1949 | Welge | 73/38 |
| 2,534,737 A | 12/1950 | Rose | 73/38 |
| 2,612,036 A | 9/1952 | Angona | 73/38 |
| 2,706,904 A | 4/1955 | Hertel | 73/38 |

(Continued)

FOREIGN PATENT DOCUMENTS

DE 1927171 12/1970

(Continued)

OTHER PUBLICATIONS

Jena, Akshaya K. and Gupta, Krishna M. "In-Plane Compression Porometry of Battery Separators." Journal of Power Sources 80. 1999. p. 46-52.

(Continued)

*Primary Examiner*—Hezron Williams
*Assistant Examiner*—Paul M. West
(74) *Attorney, Agent, or Firm*—Brown & Michaels, PC

(57) ABSTRACT

A sample chamber includes a movable upper chamber. The movable upper chamber includes a center bore opening to a bottom of the chamber, at least one port for introduction of gas under pressure to the center bore, and a first annular seal around the center bore. A stationary lower seat opposing the upper chamber has a center bore aligned with the upper chamber, and includes an exhaust and a second annular seal around the center bore. A test material is placed between the upper chamber and the lower seat. An actuator moves the upper chamber. When the upper chamber is moved down with the first annular seal in contact with an upper surface of a sample of the material and the second annular seal in contact with a lower surface of the sample, gas introduced to the upper chamber goes through the upper chamber and out through the exhaust.

27 Claims, 8 Drawing Sheets

U.S. PATENT DOCUMENTS

| | | | |
|---|---|---|---|
| 2,755,660 A | 7/1956 | Kammermeyer et al. ...... | 73/38 |
| 2,788,657 A | 4/1957 | Innes ............................. | 73/38 |
| 3,262,319 A | 7/1966 | Orr et al. ........................ | 73/38 |
| 3,577,767 A | 5/1971 | Stedile | |
| 4,112,738 A | 9/1978 | Turner ......................... | 13/32 R |
| 4,149,402 A | 4/1979 | Manes ....................... | 73/19.12 |
| 4,203,317 A | 5/1980 | Gupta ............................ | 73/38 |
| 4,217,336 A | 8/1980 | Maire et al. ................. | 423/448 |
| 4,489,593 A | 12/1984 | Pieters ........................... | 73/38 |
| 4,531,404 A * | 7/1985 | Phelps et al. .................. | 73/38 |
| 4,576,927 A | 3/1986 | Kuroda et al. ............... | 502/402 |
| 4,660,412 A | 4/1987 | Gupta ........................... | 73/38 |
| 4,718,270 A | 1/1988 | Storr .............................. | 73/38 |
| 4,744,240 A | 5/1988 | Reichelt ........................ | 73/38 |
| 5,151,187 A | 9/1992 | Behmann .................... | 210/607 |
| 5,263,360 A | 11/1993 | Blauch et al. ................. | 73/38 |
| 5,316,682 A | 5/1994 | Keyser et al. ............... | 210/649 |
| 5,361,627 A * | 11/1994 | Levesque ....................... | 73/73 |
| 5,373,727 A | 12/1994 | Heller et al. .................... | 73/38 |
| 5,442,950 A | 8/1995 | Unalmiser et al. ............. | 73/38 |
| 5,674,404 A | 10/1997 | Keyser et al. ............... | 210/741 |
| 5,695,818 A | 12/1997 | Soffer et al. ............. | 427/248.1 |
| 5,696,198 A | 12/1997 | Chereisky et al. .......... | 524/496 |
| 5,955,185 A | 9/1999 | Yoshino et al. .......... | 428/304.4 |
| 6,298,711 B1 * | 10/2001 | Volfkovich et al. ............ | 73/38 |
| 6,450,009 B1 * | 9/2002 | Hartikainen et al. ........... | 73/38 |
| 6,568,282 B1 * | 5/2003 | Ganzi ...................... | 73/861.42 |
| 2003/0066339 A1 * | 4/2003 | Chavdar ........................ | 73/38 |

FOREIGN PATENT DOCUMENTS

| | | | |
|---|---|---|---|
| DE | 3312729 A1 | 10/1984 | |
| DE | 19858338 | 12/1997 | |
| EP | 0139202 | 5/1985 | |
| EP | 0831318 | 3/1998 | |
| RU | 1807341 | 4/1993 | ..................... 73/38 |
| SU | 229002 | 2/1969 | ..................... 73/38 |
| SU | 853492 | 8/1981 | ..................... 73/38 |
| SU | 1118900 | 10/1984 | ..................... 73/38 |
| SU | 1130772 | 12/1984 | ..................... 73/38 |

OTHER PUBLICATIONS

Gupta, Vibhor and Jena, A.K.. "Substitution of Alcohol in Porometers For Bubble Point Determination." Advances in Filtration and Separation Technology. Col. 13b, 1999 p. 833-844.

Gupta, Nalini and Jena, Akshaya. "Measuring in Layers: Determining the Pore Structure of Individual Layers of Multi-Layered Ceramic Composites." Ceramic Industry, Feb. 2001. p. 28-33.

Jena, Akshaya K. and Gupta, Krishna M. "Determination of Pore Volume and Pore Distribution by Liquid Extrusion Porosimetry Without Using Mercury" Ceramic Engineering and Science Proceedings, 2002, p. 277-284.

"DWI—LB74 Porosity" http://www.dwi.twth-aachen.de/lb/74.html. Dec. 27, 1997.

Jena, Akshaya K. and Gupta, Krishna M. "A Novel Mercury Free Technique for Determination of Pore Volume, Pore Size and Liquid Permeability." P/M Science & Technology Briefs, vol. 4, No. 1. 2002. pp. 5-8.

Jena, Akshaya K. and Gupta, Krishna M. "Materials Pore-Sight Testing Pore Volume and Flow Through Porous Materials" Materials World, The Journal of the Institute of Materials, vol. 10, Num. 2, Feb. 2002.

Jena, Akshaya K. and Gupta, Krishna M. "Measurement of Pore Volume and Flow through Porous Materials", Material Testing; Jun. 2002.

Thelen, E. "Soil Permeability Tester", Franklin Institute Laboratories Notes: Franklin Inst. Journal, vol. 253, Apr. 1952, pp. 340-341.

* cited by examiner

41

AUTOMATED CLAMP-ON SAMPLE CHAMBER FOR FLOW POROMETRY AND A METHOD OF USING SAME

REFERENCE TO RELATED APPLICATIONS

This application claims an invention which was disclosed in Provisional Application No. 60/570,515, filed May 12, 2004, entitled "AUTOMATED CLAMP-ON SAMPLE CHAMBER FOR FLOW POROMETRY AND A METHOD OF USING SAME ". The benefit under 35 USC §119(e) of the United States provisional application is hereby claimed, and the aforementioned application is hereby incorporated herein by reference.

In addition, this application is a continuation in part of U.S. application Ser. No. 10/826,095, filed on Apr. 16, 2004 now abandoned, entitled "AUTOMATED CLAMP-ON SAMPLE CHAMBER FOR FLOW POROMETRY AND A METHOD OF USING SAME". The aforementioned application is hereby incorporated by reference.

BACKGROUND OF THE INVENTION

1. Field of the Invention

The invention pertains to the field of flow porometry. More particularly, the invention pertains to a sample chamber for flow porometry.

2. Description of Related Art

Flow Porometry is a technique for measurement of pore diameter, pore distribution and gas permeability. In this technique, a wetting liquid is allowed to spontaneously fill the pores of the sample. The pressure of a non-reacting gas on one side of the sample is gradually increased to empty the pores of the sample and allow gas flow through the empty pores. The differential pressure required to remove liquid from a pore is given by:

$$p = 4\gamma \cos \theta / D$$

where p is differential pressure, $\gamma$ is surface tension of the wetting liquid, $\theta$ is the contact angle of the wetting liquid on pore surface and D is pore diameter. The differential pressure of the gas on the sample and the gas flow rates are measured. The differential pressure and gas flow rates through the dry sample with all of its pores open are also measured. The differential pressure yields the pore diameter. The differential pressure and gas flow rates through wet and dry samples yield the largest pore diameter, the mean flow pore diameter, the distribution of gas flow rate over pore diameter and gas permeability. This technique is used in industry for characterization of through pores, which are very important for various kinds of filtration applications in many industries, including chemical technology, biotechnology, food technology and nonwovens.

The PMI Capillary flow porometer (41), shown in FIG. 5, is a flow porometer. It regulates gas pressure, increases gas pressure on samples in small increments, accurately measures pressures and flow rates, automatically executes all operations, and acquires, stores and displays data in many formats. This instrument, with state-of-the-art components, many innovative design features and complete automation is capable of giving highly accurate, reliable and reproducible data.

However, to test a material in a flow porometer, samples are normally cut from the bulk material, which results in damage to the material. This also restricts the number of tests that can be performed on the material. The test involves loading the sample in the sample holder, sealing the sample to prevent leakage, measuring differential pressure and gas flow rate through the dry sample, wetting the sample, measuring differential pressure and gas flow rate through the wet sample and unloading the sample. Consequently, test time is often considerable and operator skill is important.

Therefore, there is the need in the art for a sample holder that overcomes the shortcomings of the prior art. More specifically, there is a need in the art for a fully automated sample chamber, which allows a sample to be loaded without cutting the bulk test material, and allows testing to be repeated without removing the bulk material. There is also a need in the art for sample chambers that prevent any leak due to radial gas flow through the sample, permit automated application of adequate pressure on o-rings to avoid leak and reduce test time, allow automatic sample wetting for reducing test duration, and permit measurement of pressure of turbulent free gas close to the sample to improve accuracy.

SUMMARY OF THE INVENTION

A sample chamber includes a movable upper chamber. The upper chamber includes a center bore opening to a bottom of the chamber, at least one port for introduction of gas under pressure to the center bore, a port for a pressure transducer, a tube for adding wetting liquid, and a first annular seal around the center bore. A stationary lower seat opposes the upper chamber and has a center bore aligned with the upper chamber. The lower seat includes an exhaust and a second annular seal around the center bore. A material to be tested is placed between the upper chamber and the lower seat. An actuator moves the upper chamber. When the upper chamber is moved down with the first annular seal in contact with an upper surface of a sample of the material and the second annular seal in contact with a lower surface of the sample, gas introduced to the upper chamber is constrained to go through the upper chamber and out through the exhaust.

A method of performing flow porometry uses the sample chamber, and includes the steps of placing a sheet of material between the upper chamber and the lower seat, moving the upper chamber down, applying pressure with the actuator until the first annular seal and the second annular seal create a gas-tight seal around the sample, and performing at least one flow porometry test by introducing gas through the port.

An apparatus for performing flow porometry includes a sample chamber. The sample chamber includes a movable upper chamber. The upper chamber includes a center bore opening to a bottom of the chamber, at least one port for introduction of gas under pressure to the center bore and a first annular seal around the center bore. A stationary lower seat opposes the upper chamber and has a center bore aligned with the upper chamber. The lower seat includes an exhaust and a second annular seal around the center bore. A material to be tested is placed between the upper chamber and the lower seat. An actuator moves the upper chamber. When the upper chamber is moved down with the first annular seal in contact with an upper surface of a sample of the material and the second annular seal in contact with a lower surface of the sample, gas introduced to the upper chamber is constrained to go through the upper chamber and out through the exhaust. The apparatus also includes a plurality of sensors for measuring flow and differential pressure, and a source of gas.

In one embodiment, a flexible tube is connected to a hollow chamber to introduce gas that can flow through the sample. In another embodiment, the flexible tube is connected to the top of a hollow tubular piston rod to bring the gas from the top rather than from the side. In another embodiment, the apparatus includes an insert and a removable spacer in the opening of the lower seat. The spacer is removed to accommodate thick or rigid samples.

DETAILED DESCRIPTION OF THE INVENTION

Figure 1:
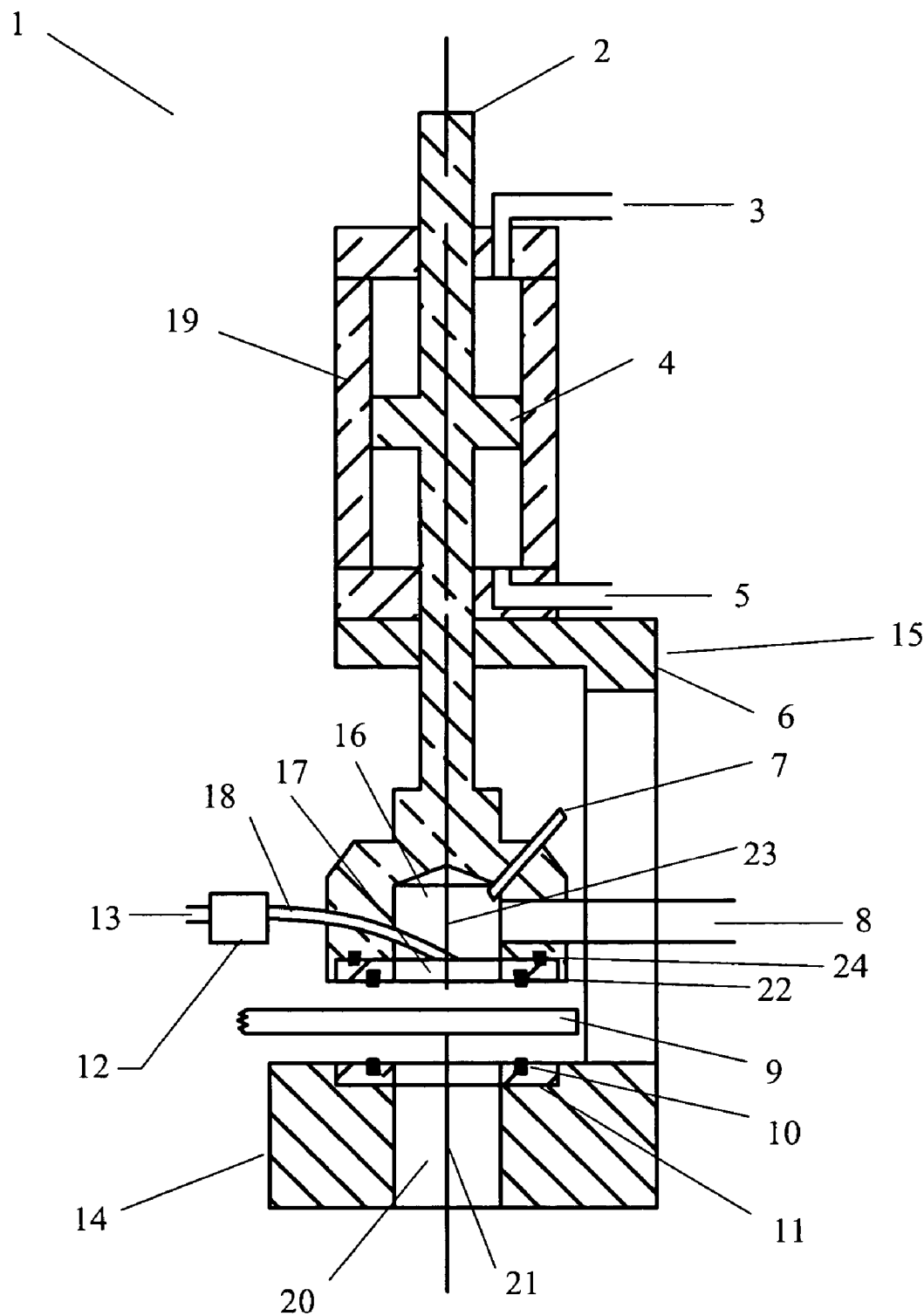
FIG. 1 shows a sample chamber in an embodiment of the present invention.
Figure 2:
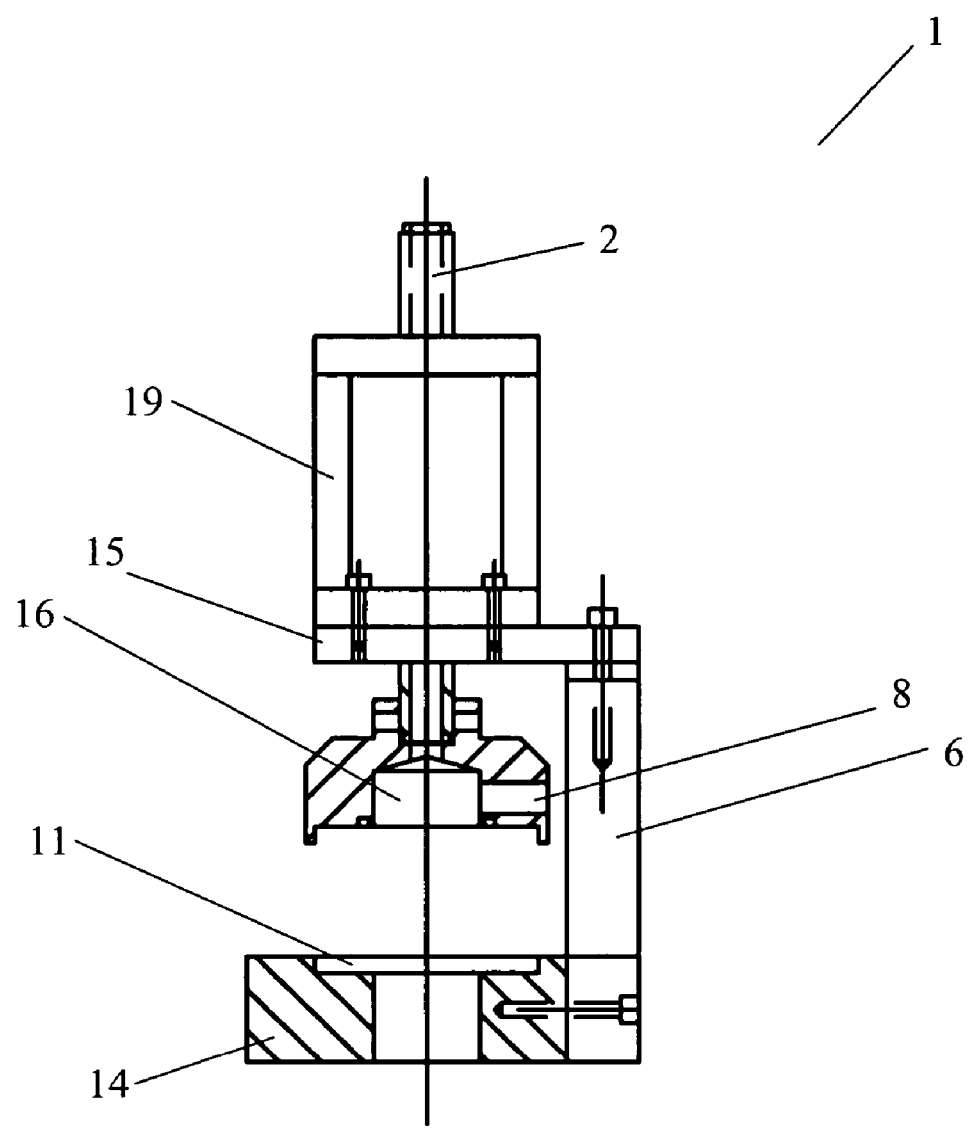
FIG. 2 shows a schematic of the sample chamber of FIG. 1.

One embodiment of the sample holder or sample chamber (1) of the present invention is illustrated in FIGS. 1 and 2. A substantially C-shaped support (6) preferably has as a part of its bottom (14) an adapter plate (11), which is preferably flat, containing an annular seal (10), which is preferably an O-ring seal or a gasket seal, and an opening (20) for the air to escape. The adapter plates are replaceable. Adapters containing different size O-rings allow the sample chamber (1) to test different sample areas. High porosity materials may require smaller areas to be tested. Also, homogeneity of a material could be evaluated by testing different areas. The bottom (14) preferably forms the stationary lower seat of the sample chamber (1). The test material (9), also known as the bulk material, to be tested is placed on the adapter (11). It is not necessary to cut a sample out of the test material (9) before the test material (9) is placed in the chamber (1).

The top part (15) of the support (6) allows an actuator, which is shown as a piston rod (2) in the figures, to move up or down. Other actuators include, but are not limited to, a rack and pinion, or a motor. Other mechanical and electrical means of moving the upper part of the sample chamber may alternatively be used. Because pressurized air is used in flow porometry, the air pressure-cylinder system shown in the figures is preferred. At the bottom of the piston rod (2) is a hollow chamber (16) and an adapter (17) similar to the one on the bottom part of the support (6). The hollow chamber (16) has a center bore (23). An annular seal (22), which is preferably an O-ring seal or a gasket seal, is also present on the bottom side of the adapter. Another annular seal (24), which is preferably an O-ring seal or a gasket seal, is present on the topside of the adapter to prevent any leak between the adapter and the piston. Other seals for any of the annular seals (10), (22) or (24) include, but are not limited to, knife-edges and glue. O-ring seals and gasket seals are preferred, because application of pressure on flexible O-rings and gaskets effectively seal many materials without damaging them.

The hollow chamber (16) and the annular seals (22) and (24) preferably form the upper movable chamber of the sample chamber. The bottom (14) of the C-shaped support opposes the hollow chamber (16) with a center bore (21) aligned with the chamber (16). The exhaust opening (20) is preferably at least as wide as the hollow chamber (16). When the upper movable chamber is moved down until the annular seal (22) is in contact with an upper surface of a sample and the second annular seal (10) is in contact with a lower surface of the sample, gas introduced to the upper chamber is constrained to go through the upper chamber and out through the exhaust (20).

A flexible tube (8) is connected to the hollow chamber (16) to introduce gas that can flow through the sample. In an alternative embodiment, as shown in the sample chamber (62) of FIG. 6, the flexible tube (60) is connected to the top of a hollow tubular piston rod (61) to bring the gas from the top rather than from the side. This arrangement has the advantage of reducing turbulence in tests requiring high flow.

A pressure transducer (7) is preferably connected to the hollow chamber (16) (FIG. 1) to measure pressure close to the sample so that errors due to pressure drops in the flexible tube (8) are avoided. The exhaust (20) is always at atmospheric pressure. In order to minimize errors due to fluctuations in atmospheric pressure, differential pressure transducers with sensors both below and above the sample are alternatively or additionally used.

Pressure of the test gas tends to reduce pressure on the O-rings. The porometer is programmed to compensate for the test gas pressure by changing the gas pressure on the top of the cylinder and to maintain a constant pressure on the O-rings. This function is particularly important for low porosity samples.

Figure 5:
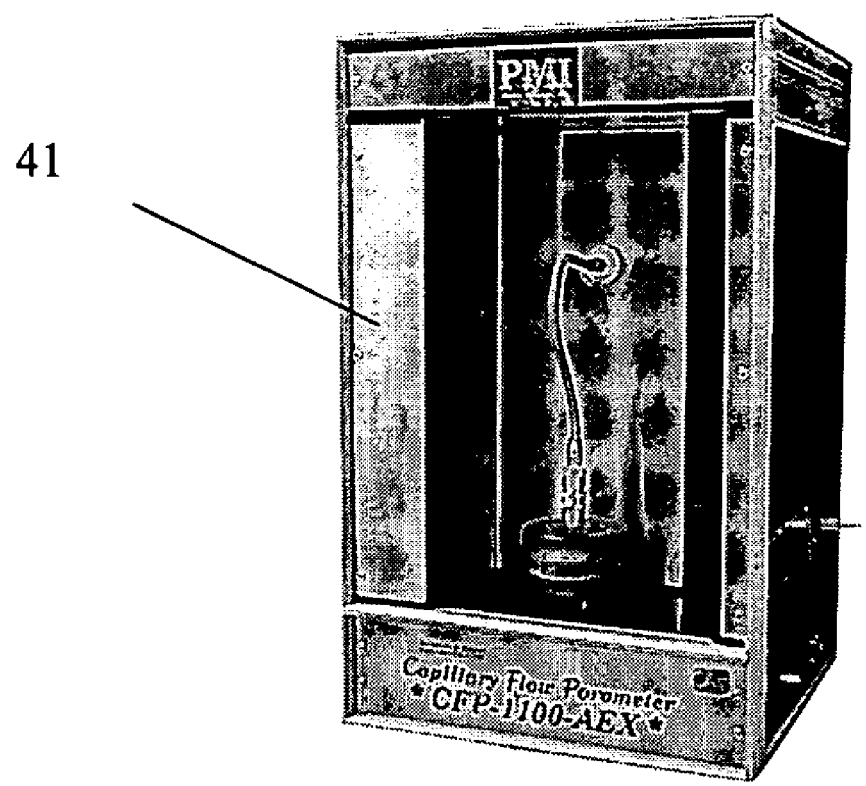
FIG. 5 shows a PMI flow porometer, used in an embodiment of the present invention.

The hollow chamber (16) contains a small tube (18) through which wetting liquid (13) is added to the sample. A valve (12) connected to the tube (18) allows measured quantities of wetting liquid (13) to be discharged. The piston rod (2) passes through a housing, which is shown as a cylinder (19) in the figures, and contains a piston (4) that moves up or down inside the cylinder (19). Openings on the top (3) and bottom (5) of the cylinder (19) are used for introducing pressurized gas. The pressurized gas inlet at the top (3) is used to move the piston (4) down, and the pressurized gas inlet at the bottom (5), is used to move the piston (4) up. The pressure of the gas introduced through the gas inlet (3) is preset to obtain a desired pressure on the O-rings and prevent sideways flow. The sample chamber (1) is preferably connected to a flow porometer, like the PMI Capillary Flow Porometer (41) shown in FIG. 5, which introduces the pressurized gas, as well as measuring and recording differential pressures and flow rates through the sample, by flexible tubes and wires.

Figure 3:
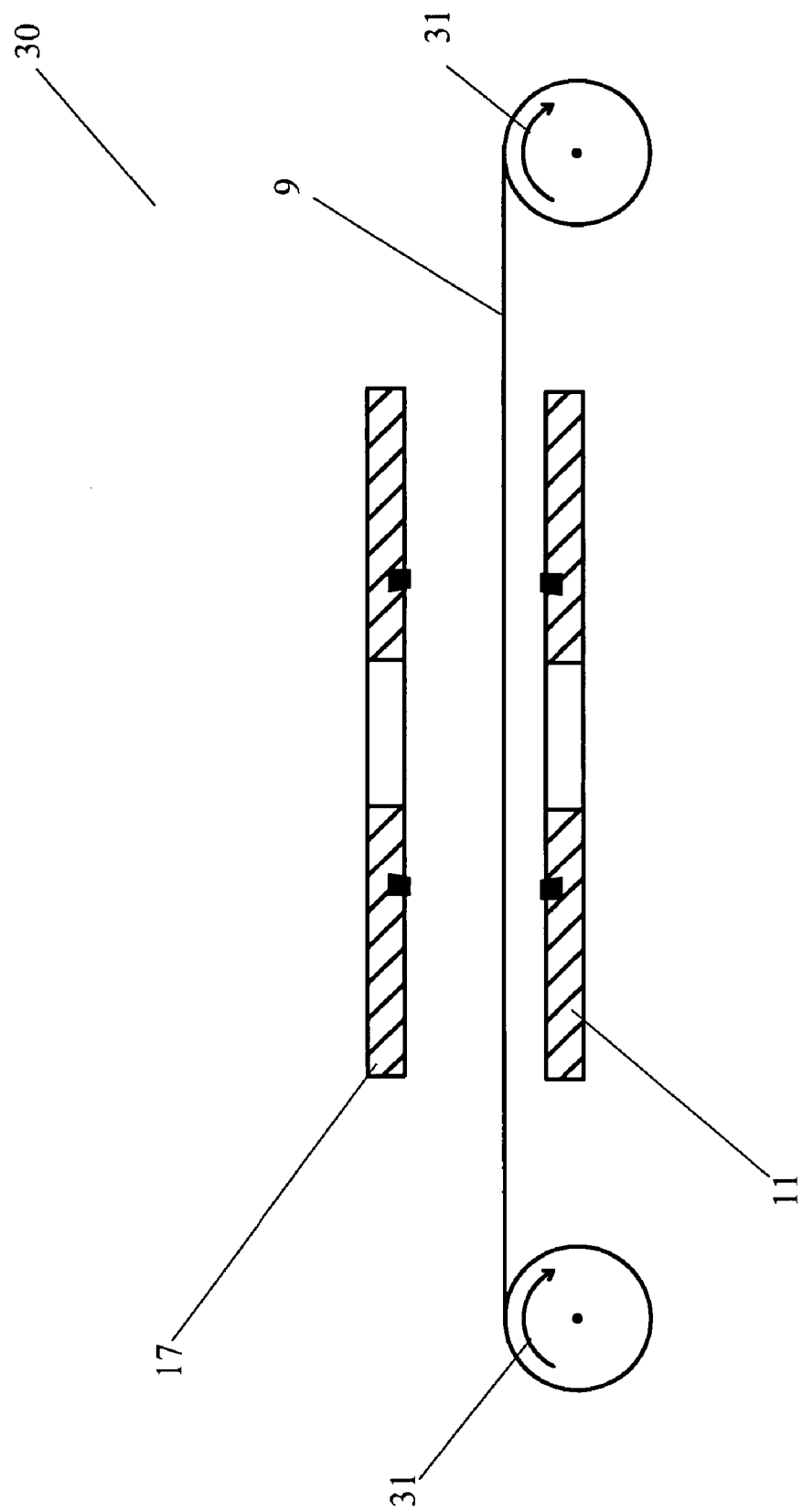
FIG. 3 shows testing of different locations by automatic feeding of material in the sample chamber.
Figure 4:
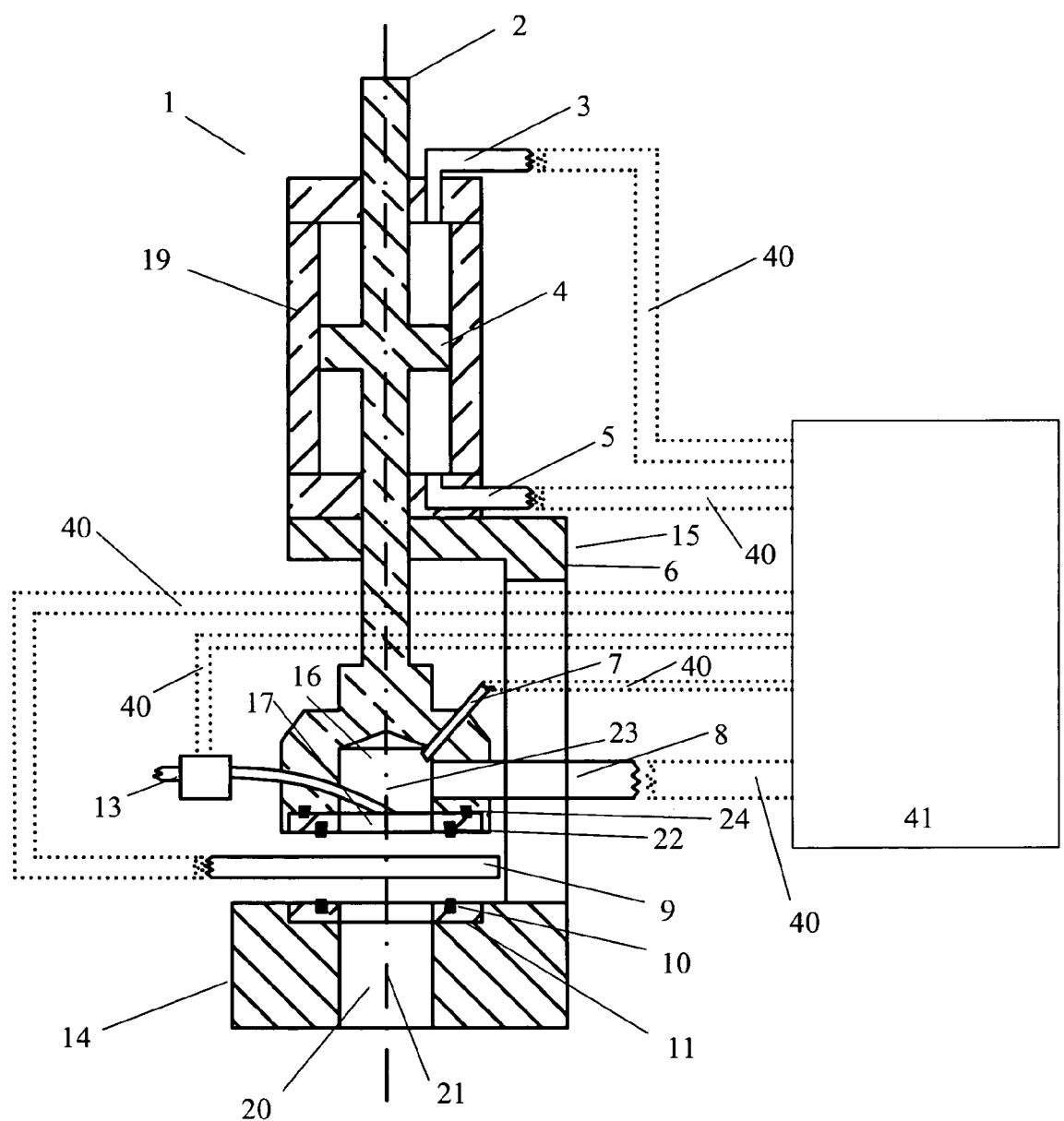
FIG. 4 shows an apparatus for flow porometry using the clamp-on sample chamber in an embodiment of the present invention.

An automatic feeding mechanism is preferably used in conjunction with the sample chamber (1) or (62) such that after each test the next test location is brought forward and moved to the top of the bottom adapter plate for testing. One such mechanism (30) is shown in FIG. 3.

Figure 6:
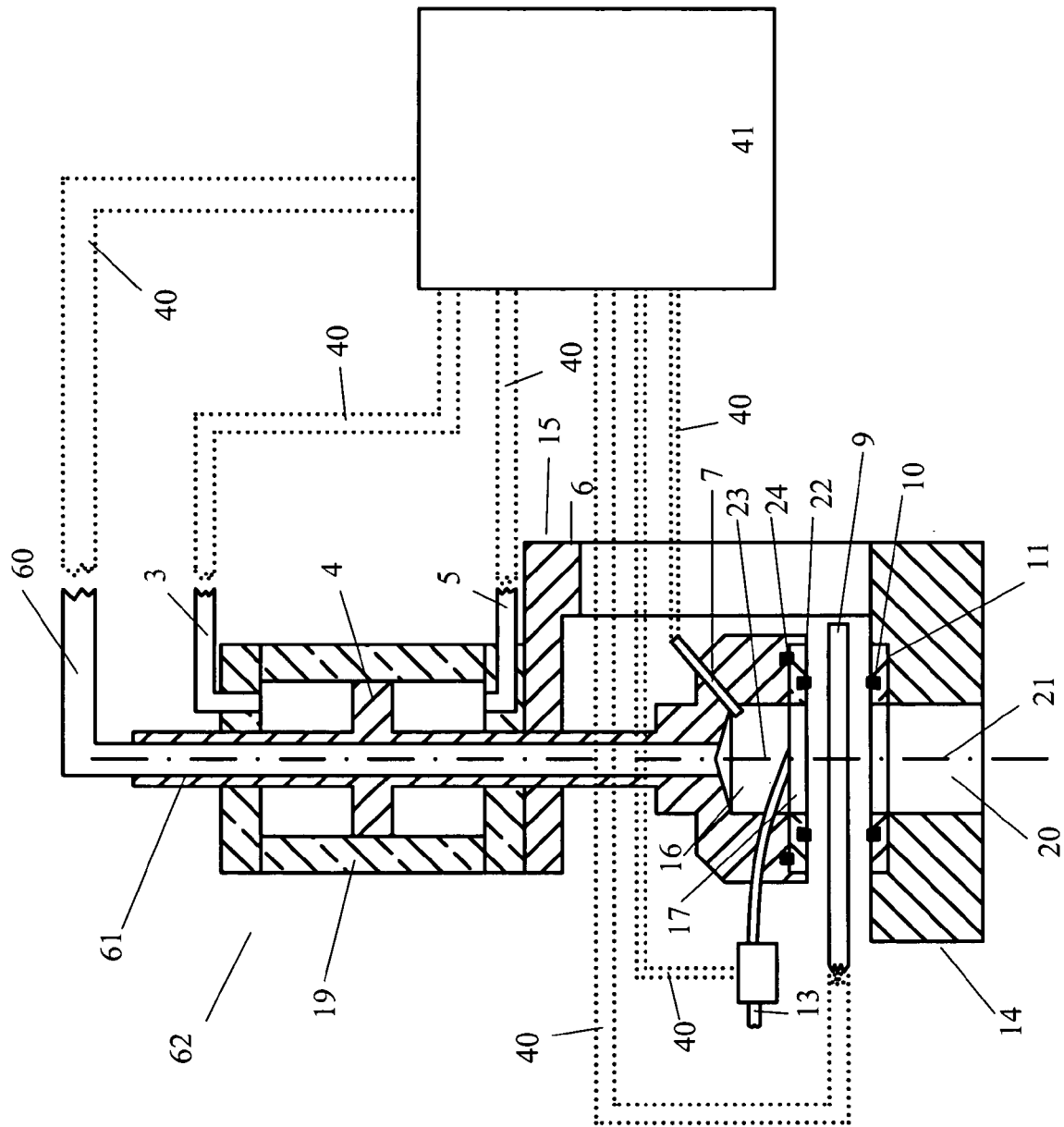
FIG. 6 shows an alternative embodiment of the apparatus of the present invention.
Figure 7:
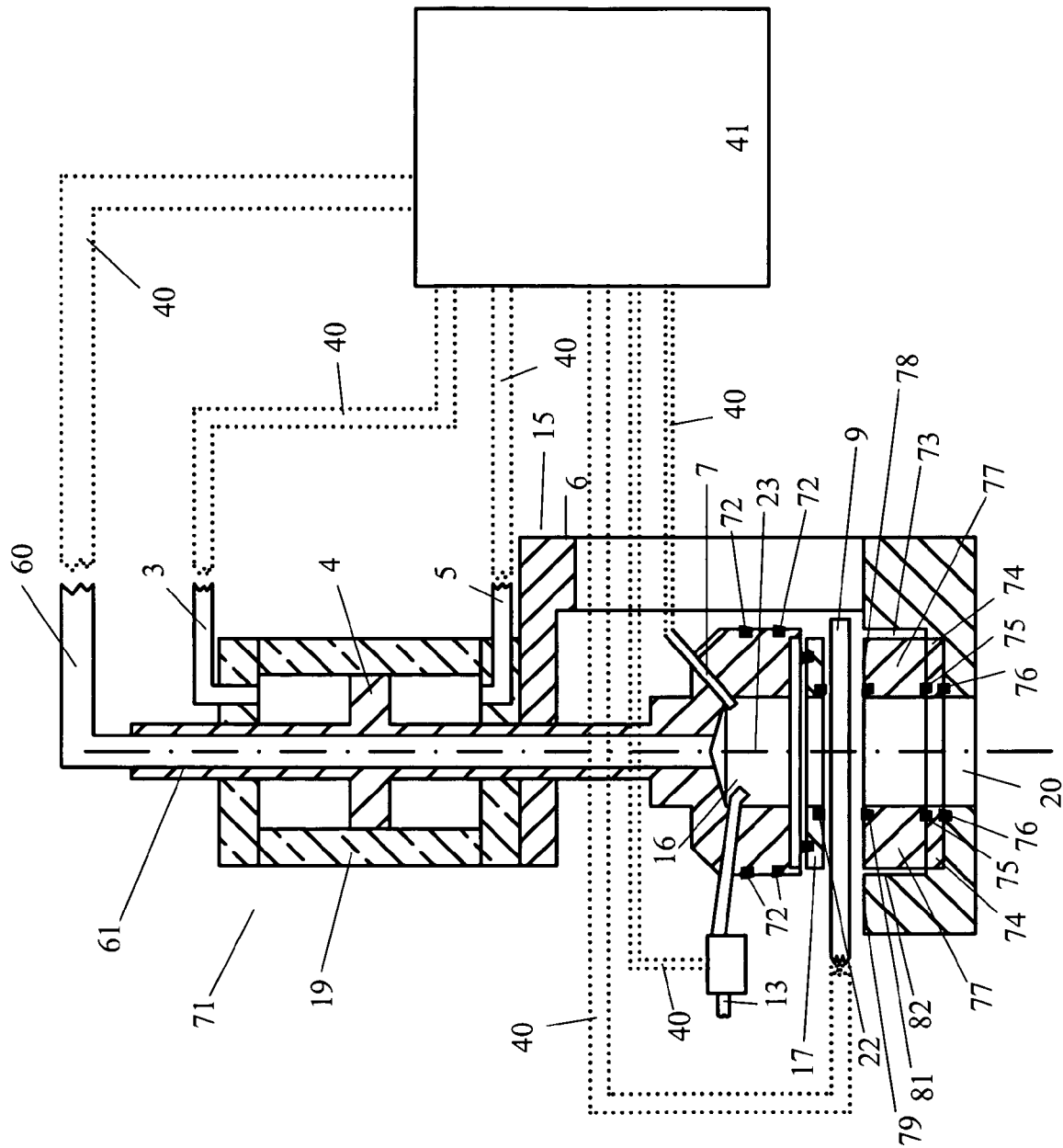
FIG. 7 shows another alternative embodiment of the apparatus of the present invention.

Referring to FIG. 7, in another embodiment, the sample chamber shown in FIG. 6 is modified so that the cylindrical upper chamber of the sample chamber (71) has annular seals (72). The annular seals (72) are preferably circumferential O-ring seals or gasket seals, but any seals that effectively seal and prevent leakage may be used. The lower seat has a cylindrical opening (73) so that the upper chamber can enter the opening and the annular seals (72) of the upper chamber make air-tight seals against the wall (82) of the opening (73).

In addition, an insert (74) with annular seals on the top (75) and bottom (76) is placed at the bottom of the opening (73) of the lower seat. The annular seals (75) and (76) are preferably O-ring seals or gasket seals, but any seals that effectively seal and prevent leakage may be used. The insert (74) is similar to the adapter (11) in the previous embodiments, however, it has an additional annular seal (76) to prevent leaks.

A removable spacer (77) is also included. When the spacer (77) is placed on the insert (74) at the bottom of the opening (73) in the lower seat, the top surface (78) of the spacer (77) is level with the top surface (79) of the lower seat.

Automatic feeding of flexible samples using the apparatus of FIG. 7 uses the insert (74) and the spacer (77). The operation of this embodiment of FIG. 7 is identical to the operation of FIG. 1 and FIG. 6 during automatic feeding. When the upper movable chamber is moved down until the annular seal (22) is in contact with an upper surface of a sample and the second annular seal (81) is in contact with a lower surface of the sample, gas introduced to the upper chamber is constrained to go through the upper chamber and out through the exhaust (20).

Figure 8:
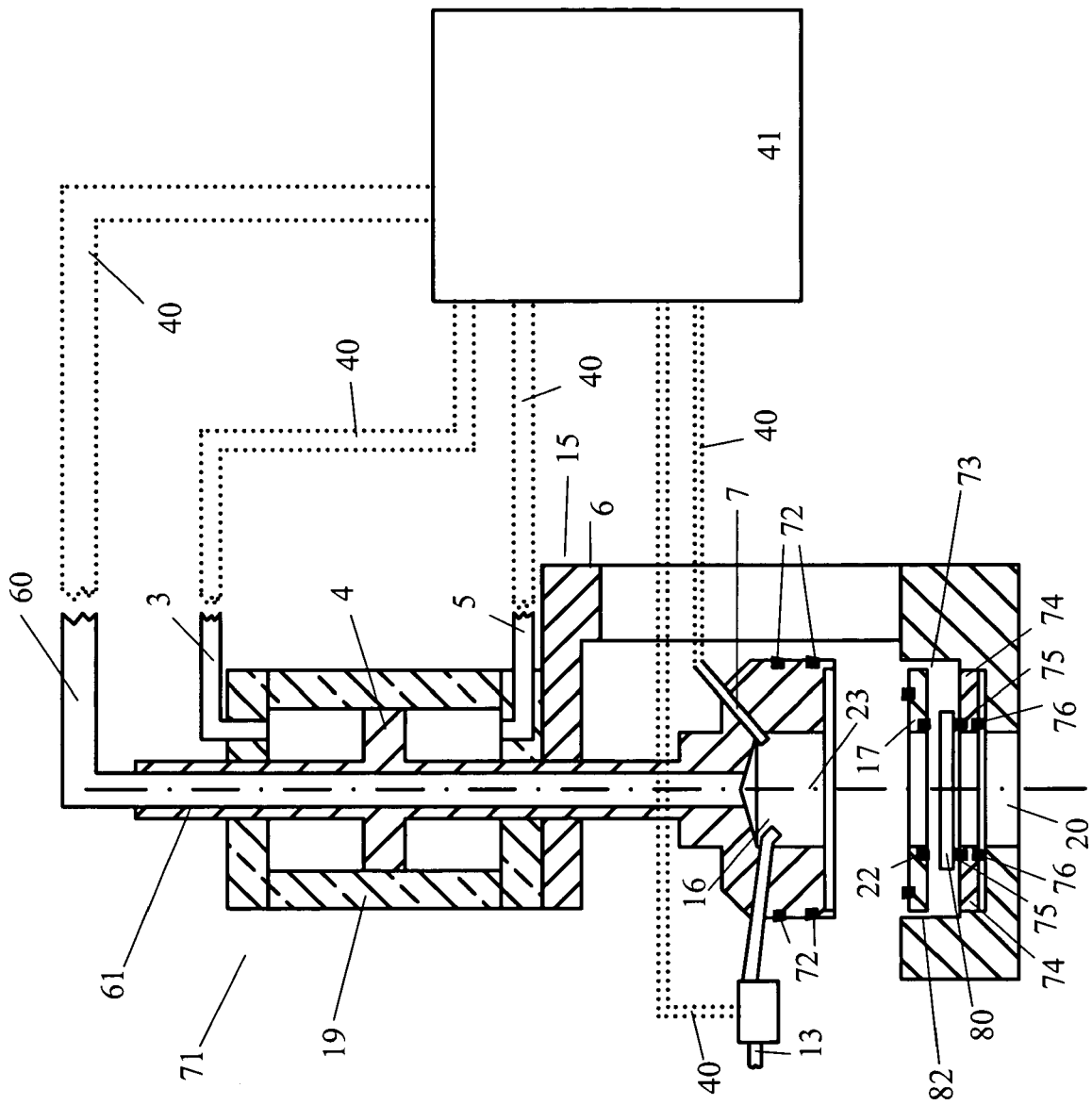
FIG. 8 shows the embodiment of FIG. 7, with the spacer removed to accommodate a thick and/or rigid sample.

Referring now to FIG. 8, for testing thick and rigid samples (80), where sidewise flow may be appreciable, the insert (74) is left inside the opening (73) in the lower seat, but the spacer (77) (see FIG. 7) is removed. The sample (80) is placed on the insert (74) and the upper chamber enters the opening (73) to clamp the sample (80). When the upper movable chamber is moved down until the annular seal (22) is in contact with an upper surface of a sample and the second annular seal (75) is in contact with a lower surface of the sample, gas introduced to the upper chamber is constrained to go through the upper chamber and out through the exhaust (20). Any sidewise flow through the sample is prevented by the annular seals (72) on the upper chamber and the annular seals (75), (76) on the insert (74).

The different embodiments of the apparatus of the present invention are particularly useful for specific applications. The first embodiment, shown in FIGS. 1 and 2, is especially useful for low flow flexible samples. The second embodiment, shown in FIG. 6, is useful for low and high flow flexible samples. The third embodiment, shown in FIGS. 7 and 8, is useful for thick, rigid or flexible samples exhibiting low or high flow. Some of the features of the three embodiments are summarized in Table 1.

| Features | FIGS. 1–2 | FIG. 6 | FIGS. 7–8 |
|---|---|---|---|
| Pressure sensing close to sample, minimal pressure drop on line | YES | YES | YES |
| Automatic addition of wetting liquid | YES | YES | YES |
| Automatic clamping of sample | YES | YES | YES |
| Pneumatically controlled pressure on o-ring on sample for better seal to prevent radial leakage of gas | YES | YES | YES |
| All operations on sample chamber performed automatically by porometer | YES | YES | YES |
| Automatic feeding of sample for test on multiple locations | YES | YES | YES, except for thick or rigid samples (when spacer is removed) |
| Entry of pressurized gas just above sample | YES | NO | NO |
| Entry of pressurized gas through wide diameter hollow piston rod to avoid turbulence | NO | YES | YES |
| No need for cutting sample | YES | YES | YES, except for thick or rigid samples (when spacer is removed) |
| Cylindrical upper chamber with circumferential O-rings enters a cylindrical opening in the lower seat and makes air tight seals against the opening to present sidewise flow | NO | NO | YES |
| Insert in the lower seat with O-rings both above and below to prevent any leaks | NO | NO | YES |

An apparatus for performing flow porometry using the clamp-on sample chamber is shown in FIGS. 4 and 6–8. The apparatus includes any of the sample chambers (1), (62) and (71) discussed above. A gas supply source supplies gas to the porometer (41). A flow sensor is preferably included in the porometer (41) to regulate the flow of gas into the sample chamber (1). Wetting liquid (13) is also introduced into the sample chamber (1). A pressure sensor (7) senses the pressure above the sample. Although not shown, in an alternative embodiment, a differential pressure sensor replaces the pressure sensor (7). The differential pressure sensor senses both the pressure above the sample and the pressure below the sample to determine a differential pressure. The sensors and the sample chamber are all preferably operatively connected to the porometer (41), which controls the apparatus. These connections (40) are shown by dotted lines in the figures. The porometer (41) fully automates the apparatus.

A method of the present invention uses the novel sample chambers (1), (62), or (71) described above, to perform the following steps:

(1) Loading the test material without cutting out a sample such that the test location is on the adapter. For thick and/or rigid samples, the sample may need to be cut, and the sample chamber (71) (without the spacer (77)) is preferably used.

(2) Sealing the material by introducing adequately pressurized gas at the top of the cylinder.

(3) Measuring differential pressure and flow rate through the dry sample.

(4) Wetting the sample.

(5) Measuring the differential pressure and flow rate through the wet sample.

(6) Unloading the sample.

(7) Repeating the procedure for the next test.

The method includes the steps of placing a sheet of material between the upper chamber and the lower seat, moving the upper chamber down, and applying pressure with the actuator until the first annular seal and the second annular seal create a gas-tight seal around the sample, and performing at least one flow porometry test by introducing gas through the port.

As an example, the method is described here with respect to the sample chamber shown in FIGS. 1 and 2. The material (9) to be tested is first placed on the top of the adapter (11) on the bottom (14) of the support (6). The porometer (41) introduces pressurized gas (3) to the top of the cylinder (19). The piston (4) and the piston rod (2) are forced to come down. The adapter (17) at the bottom of the piston (4)

presses on the O-ring (10) below the sample and seals the sample for sideways gas flow. The pressure on the O-ring (10) for obtaining a good seal is controlled by adjusting the pressure of the gas (3) introduced to the top of the cylinder (19). The porometer (41) then allows gas to be introduced (8) to the hollow chamber (16) in the piston rod (2). The gas flows through the sample and escapes through the opening at the bottom part (14) of the support (6). The porometer (41) measures and records differential pressures and flow rates through the dry sample.

Once this part of the test is done, the porometer (41) reduces gas pressure in the sample chamber to zero differential pressure and adds a predetermined amount of wetting liquid (13) to the sample. The porometer (41) then increases gas pressure and measures differential pressures and flow rates through the wet sample. Once the test is done, the porometer (41) releases pressure on the sample and then introduces pressurized gas at the bottom (5) of the cylinder (19) to raise the piston (4) and the piston rod (2). The piston rod (2) lifts the adapter (17) off of the test material (9). The material (9) is moved for the test to be performed at another location of the test material (9).

An automatic feeding mechanism (30), shown in FIG. 3, is preferably used in conjunction with the sample chamber (1), (62), or (71) such that after each test the next test location is brought forward and moved to the top of the bottom adapter plate for testing. Once a test is complete, the porometer (41) automatically activates the feeding mechanism (30) to move (31) the next test location to proper positions and continues with the test procedure at the new location. In this example, the feeding mechanism moves (31) a roll of test material (9). After the actuator lifts the adapter off the test material, an electrical switch is turned on to activate the motor that drives the roll of bulk material. The motor is programmed to unroll the product and advance it by an amount necessary to move the next test location to test position. Thus, a large number of tests can be automatically performed.

The chamber of the present invention is fully automated. The feeding mechanism used in conjunction with the chamber can completely eliminate the need for human intervention. Results are objective, accurate and reliable. The time taken for a test is small. Operator involvement and the required operator skills are minimal. Large volume of testing could be automatically, quickly and efficiently performed in a cost effective manner without damaging or wasting any material.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A sample chamber for flow porometry, comprising:
   a movable upper chamber comprising a center bore opening to a bottom of the chamber, at least one port for introduction of gas under pressure to the center bore and a first annular seal around the center bore;
   a stationary lower seat opposing the upper chamber with a center bore aligned with the upper chamber, comprising an exhaust and a second annular seal around the center bore, wherein a material to be tested is placed between the upper chamber and the lower seat;
   an actuator for moving the upper chamber, wherein when the upper chamber is moved down with the first annular seal in contact with an upper surface of a sample of the material and the second annular seal in contact with a lower surface of the sample, gas introduced to the upper chamber is constrained to go through the upper chamber and out through the exhaust; and
   at least one wetting port for introducing wetting liquid to the sample chamber.

2. The sample chamber of claim 1, wherein the actuator is selected from the group consisting of a pneumatically operated piston; a rack and pinion; and a motor.

3. The sample chamber of claim 1, further comprising a pressure transducer, connected to the center bore opening of the upper chamber, which measures pressure close to the sample.

4. The sample chamber of claim 1, further comprising a valve connected to the wetting port, which regulates a quantity of wetting liquid being discharged into the sample.

5. The sample chamber of claim 1, wherein the at least one port comprises a pressure port for introducing test gas under controlled pressure.

6. The sample chamber of claim 5, wherein gas is introduced into the sample chamber from a top of the sample chamber.

7. The sample chamber of claim 5, wherein gas is introduced in the sample chamber from a side of the sample chamber.

8. The sample chamber of claim 1, further comprising a feeding mechanism, which moves the material in the sample chamber after flow porometry has been performed at a location on the sample.

9. The sample chamber of claim 1, wherein the first annular seal comprises an O-ring.

10. The sample chamber of claim 1, wherein the second annular seal comprises an O-ring.

11. The sample chamber of claim 1, wherein the upper chamber further comprises an adapter plate located at a bottom of the upper chamber.

12. The sample chamber of claim 1, wherein the lower seat further comprises an adapter plate upon which the material to be tested is placed.

13. The sample chamber of claim 1, further comprising a removable spacer having a single central opening having a diameter that is the same as a diameter of the exhaust and comprising a first seal at a top of the removable spacer and a second seal at a bottom of the removable spacer, wherein the removable spacer fits into a cylindrical opening of the stationary lower seat such that a top surface of the removable spacer is level with a top surface of the stationary lower seat when the removable spacer is located in the cylindrical opening.

14. The sample chamber of claim 13, wherein the movable upper chamber further comprises a third annular seal located circumferentially around the movable upper chamber, such that, when the removable spacer is removed from the sample chamber, the third annular seal makes a seal with a wall of the cylindrical opening when the movable upper chamber enters the cylindrical opening.

15. A method of performing flow porometry, using a sample chamber comprising a movable upper chamber comprising a center bore opening to a bottom of the chamber, at least one port for introduction of test gas under pressure to the center bore and a first annular seal around the center bore, a stationary lower seat opposing the upper chamber with a center bore aligned with the upper chamber, comprising an exhaust and a second annular seal around the center bore, wherein a material to be tested is placed between the upper chamber and the lower seat; and, an actuator for moving the upper chamber, wherein when the upper chamber is moved down with the first annular seal in contact with an upper surface of a sample of the material and the second annular seal in contact with a lower surface of the sample, test gas introduced to the upper chamber is constrained to go through the upper chamber and out through the exhaust, comprising the steps of:
   a) placing a sheet of material between the upper chamber and the lower seat;
   b) moving the upper chamber down, and applying pressure with the actuator until the first annular seal and the second annular seal create a gas-tight seal around the sample; and
   c) performing at least one flow porometry test by introducing gas through the port;
   d) measuring a first differential pressure and a first flow rate through the sample;
   e) reducing the first differential pressure to zero;
   f) wetting the sample without unloading the sample from the sample chamber;
   g) measuring a second differential pressure and a second flow rate through the sample; and
   h) unloading the sample.

16. The method of claim 15, wherein step d) comprises the substeps of:
   i) introducing gas into the upper chamber;
   ii) allowing the gas to flow through the sample and out the exhaust; and
   iii) measuring the first differential pressure and the first flow rate.

17. The method of claim 15, wherein step g) comprises the substeps of:
   i) introducing test gas into the upper chamber at a different pressure;
   ii) allowing the gas to flow through the sample and out the exhaust; and
   iii) measuring the second differential pressure and the second flow rate.

18. The method of claim 15, further comprising the step of repeating steps (a) through (h).

19. The method of claim 15, further comprising the step of i) moving the material to perform a test on another part of the material.

20. The method of claim 19, wherein step i) is performed using a feeding mechanism.

21. The method of claim 15, wherein the actuator is pneumatically operated.

22. An apparatus for performing flow porometry using a clamp-on sample chamber, comprising:
   a) a sample chamber, comprising:
     a movable upper chamber comprising a center bore opening to a bottom of the chamber, at least one port for introduction of test gas under pressure to the center bore and a first annular seal around the center bore;
     a stationary lower seat opposing the upper chamber with a center bore aligned with the upper chamber, comprising an exhaust and a second annular seal around the center bore, wherein a material to be tested is placed between the upper chamber and the lower seat;
     an actuator for moving the upper chamber, wherein when the upper chamber is moved down with the first annular seal in contact with an upper surface of a sample of the material and the second annular seal in contact with a lower surface of the sample, test gas introduced to the upper chamber is constrained to go through the upper chamber and out through the exhaust; and
     at least one wetting port for introducing wetting liquid to the sample chamber;
   b) a plurality of sensors for measuring flow and differential pressure; and
   c) a source of gas.

23. The apparatus of claim 22, further comprising a flow porometer coupled to the sample chamber, wherein the porometer includes at least one of the sensors and a plurality of controllers, for automating the apparatus.

24. A sample chamber for flow porometry, comprising:
   a movable upper chamber comprising a center bore opening to a bottom of the chamber,
     at least one port for introduction of test gas under pressure to the center bore and a first annular seal around the center bore;
   a stationary lower seat opposing the upper chamber with a center bore aligned with the upper chamber, comprising an exhaust and a second annular seal around the center bore, wherein a material to be tested is placed between the upper chamber and the lower seat;
   an actuator for moving the upper chamber, wherein when the upper chamber is moved down with the first annular seal in contact with an upper surface of a sample of the material and the second annular seal in contact with a lower surface of the sample, test gas introduced to the upper chamber is constrained to go through the upper chamber and out through the exhaust; and
   a feeding mechanism, which moves the material in the sample chamber after flow porometry has been performed at a location on the sample.

25. An apparatus for performing flow porometry using a clamp-on sample chamber, comprising:
   a) a sample chamber, comprising:
     a movable upper chamber comprising a center bore opening to a bottom of the chamber, at least one port for introduction of test gas under pressure to the center bore and a first annular seal around the center bore;
     a stationary lower seat opposing the upper chamber with a center bore aligned with the upper chamber, comprising an exhaust and a second annular seal around the center bore, wherein a material to be tested is placed between the upper chamber and the lower seat;
     an actuator for moving the upper chamber, wherein when the upper chamber is moved down with the first annular seal in contact with an upper surface of a sample of the material and the second annular seal in contact with a lower surface of the sample, test gas introduced to the upper chamber is constrained to go through the upper chamber and out through the exhaust; and
     a feeding mechanism, which moves the material in the sample chamber after flow porometry has been performed at a location on the sample;
   b) a plurality of sensors for measuring flow and differential pressure; and
   c) a source of gas.

26. A method of performing flow porometry, using a sample chamber comprising a movable upper chamber comprising a center bore opening to a bottom of the chamber, at least one port for introduction of test gas under pressure to the center bore and a first annular seal around the center bore, a stationary lower seat opposing the upper chamber with a center bore aligned with the upper chamber, comprising an exhaust and a second annular seal around the center bore, wherein a material to be tested is placed between the upper chamber and the lower seat; and, an actuator for moving the upper chamber, wherein when the upper chamber is moved down with the first annular seal in contact with an upper surface of a sample of the material and the second annular seal in contact with a lower surface of the sample, test gas introduced to the upper chamber is constrained to go through the upper chamber and out through the exhaust, comprising the steps of:

a) placing a sheet of material between the upper chamber and the lower seat;

b) moving the upper chamber down, and applying controlled pressure with the actuator until the first annular seal and the second annular seal create a gas-tight seal around the sample; and c) performing at least one flow porometry test by introducing test gas through the port; and d) moving the material to perform a test on another part of the material.

27. The method of claim 26, wherein step d) is performed using a feeding mechanism.

* * * * *